US00PP36015P3

(12) United States Plant Patent
Kleinwee

(10) Patent No.: US PP36,015 P3
(45) Date of Patent: Jul. 16, 2024

(54) ***PETUNIA* PLANT NAMED 'PEHY0081'**

(50) Latin Name: *Petunia hybrida*
Varietal Denomination: PEHY0081

(71) Applicant: SYNGENTA CROP PROTECTION AG, Basel (CH)

(72) Inventor: Theodorus Cornelis Maria Van Kleinwee, Enkhuizen (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 18/445,441

(22) Filed: Aug. 17, 2023

(65) Prior Publication Data

US 2024/0090357 P1 Mar. 14, 2024

(30) Foreign Application Priority Data

Sep. 12, 2022 (QZ) ..... PBR 2022/2064

(51) Int. Cl.
*A01H 5/02* (2018.01)
*A01H 6/82* (2018.01)

(52) U.S. Cl.
USPC ..... Plt./356.21
CPC ..... *A01H 6/824* (2018.05)

(58) Field of Classification Search
USPC ..... Plt./356.21
CPC . A01H 5/02; A01H 5/00; A01H 6/824; A01H 6/82
See application file for complete search history.

(56) References Cited

PUBLICATIONS

CPVO Register S2/S3 version 4.12.6 retrieved on Nov. 2, 2023 at https://online.plantvarieties.eu/publicConsultationDetails?registerId=20222064&denomination=pehy0081, 2 pp. (Year: 2023).*

* cited by examiner

*Primary Examiner* — June Hwu
(74) *Attorney, Agent, or Firm* — Dale Skalla

(57) ABSTRACT

A new *Petunia* plant named 'PEHY0081' particularly distinguished by its big flowers, a pink flower color with distinct veins, a rather early flowering and a semi trailing plant habit.

1 Drawing Sheet

Latin name of the genus and species of the plant claimed: *Petunia hybrida.*

Varietal denomination: 'PEHY0081'.

BACKGROUND OF THE NEW PLANT

The present invention comprises a new *Petunia*, botanically known as *Petunia hybrida*, and hereinafter referred to by the variety name 'PEHY0081'.

'PEHY0081' is a product of a planned breeding program. The new cultivar has big flowers, a pink flower color with distinct veins, a rather early flowering and a semi trailing plant habit.

'PEHY0081' originated from a hybridization made in June 2018 in a controlled breeding environment in Enkhuizen, The Netherlands. The female parent was the proprietary selection 'BA0551-2V', not patented. Compared to 'PEHY0081', it is less vigorous, a more mounding plant habit, a better branching and earlier flowering.

The male parent of 'PEHY0081' was the proprietary selection 'PETBC0194-1V', not patented. Compared to 'PEHY0081', it is more vigorous, less branching and it has a less pronounced veining in the flower.

The resulting seeds were sown in September 2018. 'PEHY0081' was selected as one flowering plant within the progeny of the stated cross in November 2018 in a controlled environment in Enkhuizen, The Netherlands.

The first act of asexual reproduction of 'PEHY0081' was accomplished when vegetative stem cuttings were propagated from the initial selection in January 2019 in a controlled environment in Enkhuizen, The Netherlands.

BRIEF SUMMARY OF INVENTION

Horticultural examination of plants grown from cuttings of the plant initiated in January 2019 and continuing thereafter, has demonstrated that the combination of characteristics as herein disclosed for 'PEHY0081' are firmly fixed and are retained through successive generations of asexual reproduction.

'PEHY0081' has not been observed under all possible environmental conditions. The phenotype may vary significantly with variations in environment such as temperature, light intensity, and day length.

A Plant Breeder's Rights for this cultivar was applied for in the European Union on Sep. 12, 2022, No. 2022/2064. 'PEHY0081' has not been made publicly available prior to the effective filing date of this application, notwithstanding any disclosure that may have been made less than one year prior to the effective filing date of this application by the inventor or another who obtained 'PEHY0081' directly from the inventor.

The following traits have been repeatedly observed and are determined to be basic characteristics of the new variety. The combination of these characteristics distinguishes this *Petunia* as a new and distinct variety.

BRIEF DESCRIPTION OF THE PHOTOGRAPHS

The accompanying photographic drawings show typical flower and foliage characteristics of 'PEHY0081' with colors being as true as possible with an illustration of this type.

Figure 1:
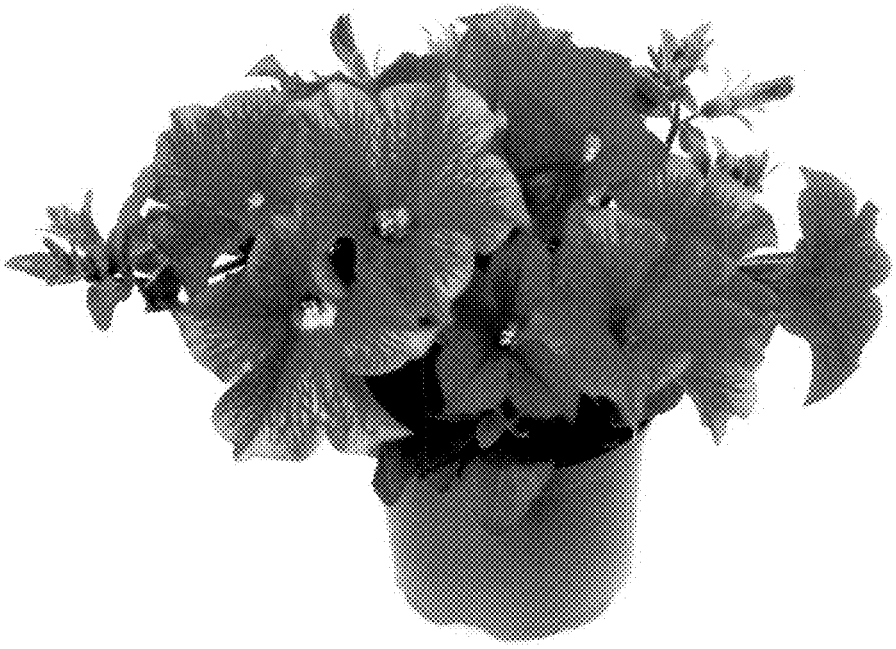
Figure 2:
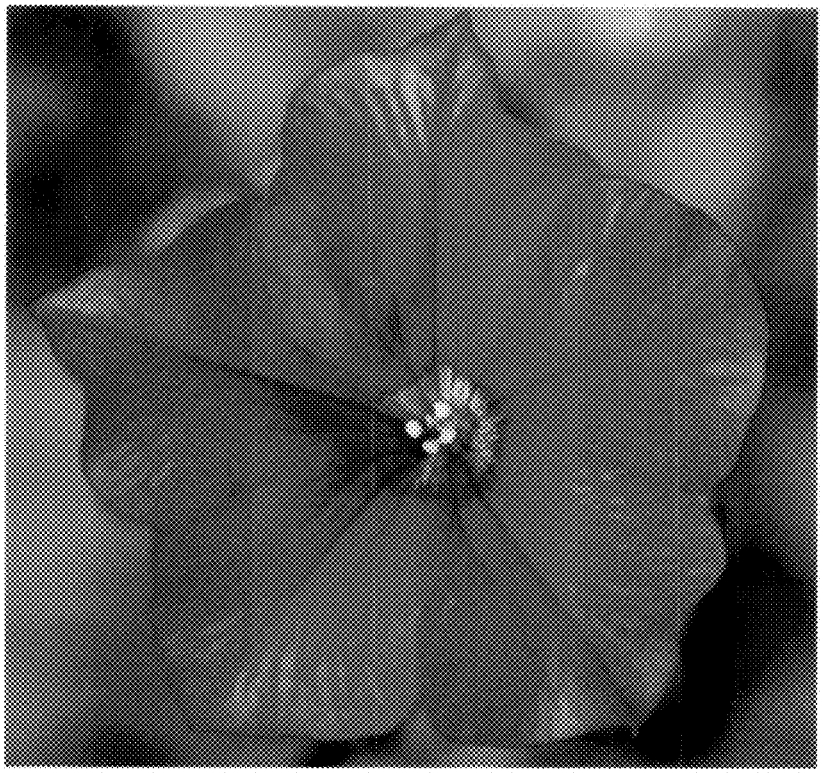

The photographic drawings show in FIG. 1 a flowering plant of the new variety and in FIG. 2 a close-up of the flowers.

DETAILED BOTANICAL DESCRIPTION

The aforementioned photographs were taken in May 2021 from plants growing indoor in 12 cm pots in Andijk, The Netherlands. These plants were approximately 12 weeks of age.

The plant descriptions and measurements were taken in July 2023 in Enkhuizen, The Netherlands on outdoor plants grown in full soil. These plants were about 16 weeks old.

Color references are made to The Royal Horticultural Society Colour Chart (R.H.S.) 2001.

TABLE 1

DIFFERENCES BETWEEN THE NEW VARIETY 'PEHY0081' AND A SIMILAR VARIETY

| | PEHY0081' | 'Surfinia ® Hot pink', Not patented |
|---|---|---|
| Branching: | Good | Rather poor |
| Flower size: | Big | Very big |
| Earliness: | Rather early | Very late |

Plant:

*Form, growth and habit.*—Semi trailing plant habit.

*Plant height.*—18 cm.

*Plant height* (*inflorescence included*).—22 cm.

*Plant diameter* (*width*).—Approximately 45 cm.

Roots:

*Number of days to initiate and produce roots.*—14 days at about 22° C.

*Type.*—Fine, fibrous, free branching.

*Color.*—RHS N158D.

Foliage:

*Arrangement.*—Alternate, simple; sometimes opposite, decussate.

*Immature leaf, color upper surface.*—RHS 137B.

*Immature leaf, color lower surface.*—RHS 137D.

*Mature leaf, color upper surface.*—RHS 137B.

*Mature leaf, color lower surface.*—RHS 137C.

*Length.*—4.0-5.0 cm.

*Width.*—1.9 cm.

*Shape.*—Ovate.

*Base shape.*—Acuminate.

*Apex shape.*—Acute.

*Margin.*—Entire.

*Texture, upper surface.*—Densely covered with short hair.

*Lower surface.*—Densely covered with short hairs.

*Color of veins, upper surface.*—RHS 137C.

*Color of veins, lower surface.*—RHS 137C.

*Petiole color.*—RHS 137C.

*Length.*—0.2 cm.

*Diameter.*—0.2 cm.

*Petiole texture.*—Densely covered with short hairs.

Stem:

*Quantity of main branches per plant.*—4-5.

*Color of stem.*—RHS 137C, RHS 147C on old stem parts.

*Length of stem.*—23 cm.

*Diameter.*—0.3-0.4 cm.

*Length of internodes.*—1.6-2.6 cm.

*Texture.*—Dense, mostly glandular short hairs.

*Color of pedicel.*—RHS 137C.

*Length of pedicel.*—2.7 cm.

*Diameter of pedicel.*—0.2 cm.

*Texture of pedicel.*—Densely covered with short hairs.

Inflorescence:

*Type.*—Flowers solitary in upper leaf axis.

*Floret type.*—Funnel-shaped; 5 lobed petals; fused at base.

*Blooming habit.*—Rather early flowering in greenhouse, flowering throughout the summer months.

*Quantity of inflorescences per plant.*—Approximately 50.

*Lastingness of individual blooms on the plant.*—About 7 days.

*Fragrance.*—Rather strong smell.

Bud (just when opening):

*Color.*—RHS N79C at top, RHS N77C towards base.

*Length.*—4.5 cm.

*Width.*—0.8 cm.

*Shape.*—Oblong.

Immature inflorescence:

*Flower horizontal diameter.*—5.5 cm.

*Color petals, upper surface.*—RHS N57B with veins RHS 61A.

*Color petals, lower surface.*—RHS 61C.

Mature flower:

*Flower horizontal diameter.*—6.0 cm.

*Flower height* (*vertical*).—4.4 cm.

*Color upper surface.*—RHS N57C with veins RHS 67A.

*Color lower surface.*—RHS 67B.

*Conspicuousness of veins.*—Very strong.

*Apex shape.*—Acuminate.

*Margin.*—Entire.

*Waviness of margin.*—Medium.

*Petal lobation.*—Weak.

*Petal texture, upper surface.*—Smooth.

*Petal texture, lower surface.*—Smooth, occasionally a short hair mainly along veins.

*Corolla tube color outside.*—RHS 54C with veins RHS 177B.

*Corolla tube color inside.*—RHS 154C deep in throat; Veins RHS 174A, RHS 87D towards petals; occasionally turning into a small ring (1-3 mm wide) on the border of throat and petals of RHS 87B.

*Size of the area of secondary color.*—Small.

*Conspicuousness of veins in tube.*—Strong.

*Corolla tube length.*—3.0 cm.

*Corolla tube texture, outside.*—Dense and short glandular hairs.

*Corolla tube texture, inside.*—Glabrous.

Calyx:

*Color of sepal, upper surface.*—RHS 137B.

*Color of sepal, lower surface.*—RHS 137C.

*Length.*—1.3 cm.

*Width.*—0.3-0.4 cm.

*Shape.*—Ensiform.

*Apex shape.*—Acute.

*Base.*—Fused.

*Margins*.—Entire.
*Texture, upper surface*.—Densely covered with short glandular hairs.
*Lower surface*.—Densely covered with short glandular hairs.

Reproductive organs:
*Pistil*.—1.
*Length*.—2.2 cm.
*Style color*.—RHS 149C.
*Style length*.—2.0 cm.
*Stigma color*.—RHS 145A, RHS 134A in center of stigma.
*Stamens*.—
*Quantity per flower*.—5.
*Color of filaments*.—RHS 157D, RHS 145D towards base.
*Length filaments*.—1.9 cm.
*Anther color*.—RHS 158B.
*Anther length*.—0.2 cm.
*Anther shape*.—Elliptical.
*Color of pollen*.—RHS 155B.
*Pollen amount*.—Abundant.
*Fertility/seed set*.—Has not been observed on this hybrid.
*Disease/pest resistance*.—Has not been observed on this hybrid.

What is claimed is:

1. A new and distinct variety of *Petunia* plant named 'PEHY0081' substantially as illustrated and described herein.

* * * * *